(12) United States Patent
Peterson et al.

(10) Patent No.: US 8,747,360 B2
(45) Date of Patent: Jun. 10, 2014

(54) ADHESIVE BACKED IV CATHETER WITH AUTO RELEASE LINER

(71) Applicant: Becton, Dickinson and Company, Franklin Lakes, NJ (US)

(72) Inventors: Bart D. Peterson, Farmington, UT (US); Marcel A. Souza, Provo, UT (US); Darin L. Peterson, Taylorsville, UT (US); Azhar J. Khan, Salt Lake City, UT (US)

(73) Assignee: Becton, Dickinston and Company, Franklin Lakes, NJ (US)

( * ) Notice: Subject to any disclaimer, the term of this patent is extended or adjusted under 35 U.S.C. 154(b) by 0 days.

(21) Appl. No.: 13/706,076

(22) Filed: Dec. 5, 2012

(65) Prior Publication Data

US 2013/0150791 A1     Jun. 13, 2013

Related U.S. Application Data

(60) Provisional application No. 61/568,082, filed on Dec. 7, 2011.

(51) Int. Cl.
A61M 5/178     (2006.01)

(52) U.S. Cl.
USPC .................................... 604/164.04

(58) Field of Classification Search
USPC .................... 604/164.04, 177–180
See application file for complete search history.

(56) References Cited

U.S. PATENT DOCUMENTS

| | | | | |
|---|---|---|---|---|
| 2,409,432 A | * | 10/1946 | Hubbard | 604/179 |
| 2,449,882 A | * | 9/1948 | Daniels | 604/179 |
| 3,160,158 A | * | 12/1964 | Rayhart | 604/179 |
| 3,167,072 A | * | 1/1965 | Hester et al. | 604/179 |
| 3,782,378 A | * | 1/1974 | Page | 128/888 |
| 4,316,461 A | * | 2/1982 | Marais et al. | 604/179 |
| 4,324,236 A | * | 4/1982 | Gordon et al. | 604/272 |
| 4,326,517 A | * | 4/1982 | Whitney et al. | 604/155 |
| 4,326,519 A | * | 4/1982 | D'Alo et al. | 604/165.04 |
| 4,362,156 A | * | 12/1982 | Feller et al. | 604/165.03 |
| 4,453,933 A | * | 6/1984 | Speaker | 604/179 |
| 4,470,410 A | * | 9/1984 | Elliott | 128/877 |
| D290,041 S | * | 5/1987 | Scott | D24/128 |
| 4,863,432 A | * | 9/1989 | Kvalo | 604/177 |
| 5,084,026 A | * | 1/1992 | Shapiro | 604/179 |
| 5,087,248 A | * | 2/1992 | Beisang, III | 604/180 |
| 6,074,368 A | * | 6/2000 | Wright | 604/179 |
| 6,086,564 A | * | 7/2000 | McLaughlin | 604/179 |
| 6,283,945 B1 | * | 9/2001 | Bierman | 604/174 |
| 6,500,154 B1 | * | 12/2002 | Hakky et al. | 604/174 |
| 6,526,981 B1 | * | 3/2003 | Rozier et al. | 128/846 |

(Continued)

*Primary Examiner* — Jason Flick
*Assistant Examiner* — Diva K Chander
(74) *Attorney, Agent, or Firm* — Jeanne Lukasavage; Craig Metcalf; Kirton McConkie

(57) ABSTRACT

Intravenous catheter devices are provided which may include one or more adhesive portions which are positioned and configured to temporarily maintain a position of a catheter assembly following catheterization. A release liner covering and protecting the adhesive portions may be automatically removed to reveal the adhesive upon withdrawal of an introducer needle of the catheter assembly. The adhesive may be configured such that a clinician may insert the catheter assembly into the patient, adjust the catheter adapter of the catheter assembly to a desired position, withdraw the introducer needle, thereby removing a protective, non-adhesive release liner from the adhesive of the positioned catheter assembly, thereby temporarily fixing the position of the catheter assembly at the desired position by contacting the exposed adhesive to the skin of the patient.

20 Claims, 3 Drawing Sheets

(56) References Cited

U.S. PATENT DOCUMENTS

| | | | |
|---|---|---|---|
| 6,953,448 B2* | 10/2005 | Moulton et al. | 604/164.01 |
| 7,198,616 B2* | 4/2007 | Mossanen-Shams et al. | 604/174 |
| 7,626,070 B2* | 12/2009 | Propp | 602/41 |
| 7,722,571 B2* | 5/2010 | Bierman et al. | 604/180 |
| 8,109,912 B2* | 2/2012 | Alferness et al. | 604/181 |
| 8,172,807 B2* | 5/2012 | Dikeman et al. | 604/180 |
| 8,197,447 B2* | 6/2012 | Wright | 604/174 |
| 8,211,064 B2* | 7/2012 | Sloan | 604/179 |
| 8,298,191 B2* | 10/2012 | Bierman et al. | 604/180 |
| 8,496,625 B2* | 7/2013 | Brugger et al. | 604/177 |
| 8,500,698 B2* | 8/2013 | Kyvik et al. | 604/174 |
| 2004/0034330 A1* | 2/2004 | Bierman et al. | 604/500 |
| 2004/0234605 A1* | 11/2004 | Cox et al. | 424/486 |
| 2005/0131353 A1* | 6/2005 | Mossanen-Shams et al. | 604/179 |
| 2005/0137496 A1* | 6/2005 | Walsh et al. | 600/561 |
| 2007/0142784 A1* | 6/2007 | Dikeman et al. | 604/174 |
| 2009/0137962 A1* | 5/2009 | Bracken et al. | 604/179 |
| 2010/0106095 A1* | 4/2010 | Vitaris et al. | 604/177 |
| 2010/0114034 A1* | 5/2010 | Wright et al. | 604/177 |
| 2010/0179481 A1* | 7/2010 | Bierman et al. | 604/177 |
| 2010/0234804 A1* | 9/2010 | Hiejima et al. | 604/110 |
| 2011/0295207 A1* | 12/2011 | Brugger et al. | 604/164.04 |

* cited by examiner

ADHESIVE BACKED IV CATHETER WITH AUTO RELEASE LINER

RELATED APPLICATION

This application claims the benefit of U.S. Provisional Patent Application No. 61/568,082 filed on Dec. 7, 2011, entitled ADHESIVE BACKED IV CATHETER WITH AUTO RELEASE LINER AND STRATEGICALLY SHAPED/PLACED ADHESIVE, which are incorporated herein by reference in their entireties.

BACKGROUND

This disclosure relates generally to intravenous catheters. More specifically, this disclosure discusses various methods and systems for incorporating adhesive portions with an automatic release liner to an intravenous catheter to permit temporary securement of the intravenous catheter to a patient.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following catheterization, the intravenous catheter assembly is secured to the patient to prevent premature and/or unintended removal of the catheter assembly. In some instances, the clinician holds the inserted catheter assembly in place by digital pressure while preparing and applying adhesive strips to the catheter assembly. This process generally requires both hands of the clinician, and therefore the clinician commonly prepares the adhesive strips prior to inserting the catheter assembly into the patient, requiring placing the adhesive strips in a temporary location while attempting to secure the catheter assembly. This temporary location placement may provide additional opportunities for infective agents to contact the catheter assembly once the adhesive strips are in place. In other instances, a first clinician catheterizes the patient while a second clinician prepares and applies the adhesive strips to secure the inserted catheter assembly, lessening the infection risk, but greatly increasing the resources and effort required to place a catheter. Thus, the process of securing the inserted catheter assembly to the patient can be time consuming, cumbersome, and in some instances, add undue risk of infection.

BRIEF SUMMARY OF THE INVENTION

This disclosure relates generally to intravenous catheters that provide simpler, more effective, and lower risk intravenous catheter placement in a patient. More specifically, this disclosure discusses various methods and systems for incorporating adhesive strips with automatically releasing liners to an intravenous catheter to permit temporary securement of the intravenous catheter to a patient.

Some intravenous catheter assemblies may include an integrated catheter securement adhesive with a release liner that is automatically removed upon proper placement of the catheter assembly. Some embodiments of catheter assemblies may include, a catheter adapter, a catheter coupled to an end of the catheter adapter, at least one adhesive portion affixed to the catheter adapter, and a release liner releasably coupled to the at least one adhesive portion. The release liner may be folded over. The catheter adapter may further include a winged extension, with the adhesive portion affixed to the winged extension. The adhesive portion may be affixed on a bottom side of the winged extension configured to contact the skin of a patient when in use. In some embodiments, at least 50% of the bottom side of the winged extension may be covered by the at least one adhesive portion. The adhesive portion may include an anti-microbial agent. Some embodiments may also include a needle shield, with a portion of the release liner permanently attached to the needle shield.

In other embodiments, catheter assemblies may include, a catheter adapter having an outer surface, an adhesive affixed to the outer surface, and a release liner releasable coupled to the adhesive. The release liner may be held in a folded configuration prior to use. The assembly may also include releasable component attached to the catheter adapter, a portion of the release liner being attached to the releasable component. The releasable component may be configured to aid in placement of the catheter adapter intravenously, and may be one of an introducer needle, a needle shield, or a needle hub.

In yet other embodiments, a catheter assembly may include, a catheter adapter having a proximal end, a distal end and a middle section extending therebetween, a securement platform coupled to the middle section and comprising an underside, an adhesive applied to the underside of the securement platform, and a release liner applied to the adhesive, the release liner having a pull tab positioned beyond the proximal end of the catheter adapter. The assembly may also include a needle shield and an introducer needle. The pull tab may be coupled to one of the needle shield and the introducer needle. In some embodiments, the adhesive may be a single-use glue, or a multiple-use glue.

BRIEF DESCRIPTION OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which.

Figure 1:
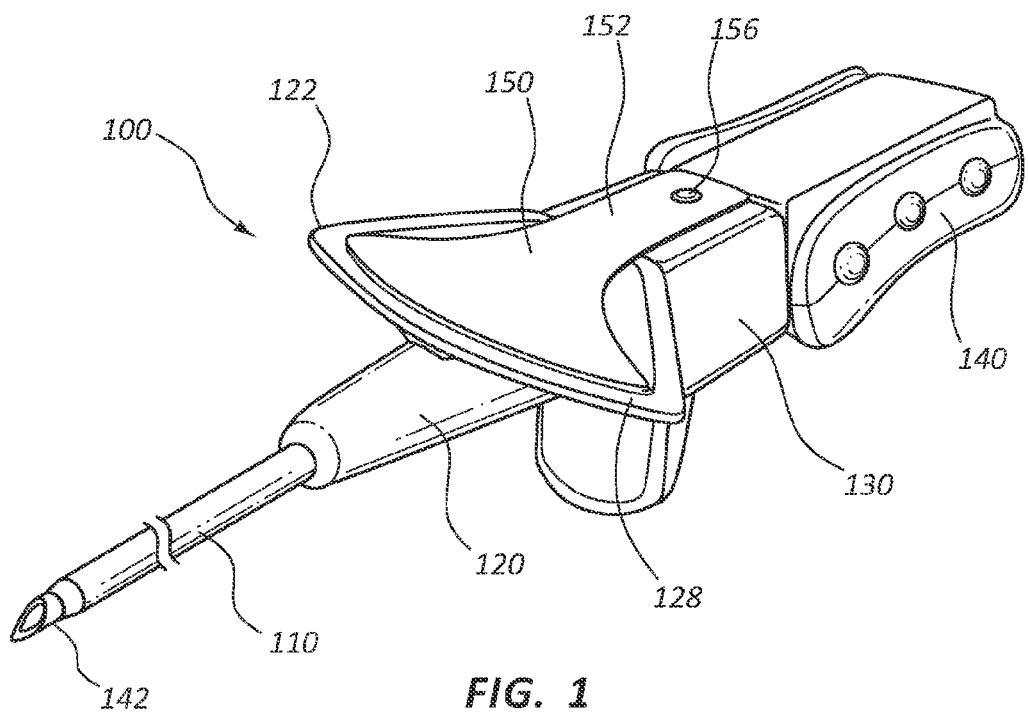
FIG. 1 illustrates a bottom perspective view of an exemplary catheter assembly having an adhesive portion and release liner.

The Figures illustrate specific aspects of exemplary intravenous catheter assemblies with an integrated catheter securement adhesive and release liner and methods for making and using such devices as described below. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity.

DETAILED DESCRIPTION OF THE INVENTION

The following description supplies specific details in order to provide a thorough understanding. Nevertheless, the skilled artisan would understand that the described intravenous catheter assemblies with an integrated catheter securement adhesive and release liner and methods of making and using them can be implemented and used without employing these specific details. Indeed, the intravenous catheter assemblies with integrated catheter securement adhesive and release liner and associated methods can be placed into practice by modifying the illustrated devices and methods and can be used in conjunction with any other apparatus and techniques conventionally used in the industry.

Generally, this disclosure is related to systems and methods for securing a catheter assembly to a patient following catheterization. In some instances, a catheter assembly may include one or more adhesive portions which are positioned and configured to temporarily maintain a position of a catheter assembly following catheterization. A release liner covering and protecting the adhesive portions may be automatically removed to reveal the adhesive upon withdrawal of an introducer needle of the catheter assembly. The adhesive may be configured such that a clinician may insert the catheter assembly into the patient, adjust the catheter adapter of the catheter assembly to a desired position, withdraw the introducer needle, thereby removing a protective, non-adhesive release liner from the adhesive of the positioned catheter assembly, and temporarily fix the position of the catheter assembly at the desired position by contacting the exposed adhesive to the skin of the patient. In some instances, the exposed adhesive temporarily fixes the position of the catheter assembly, thereby allowing the clinician to gather and apply the final materials for longer-term securement of the catheter assembly to the patient. In other instances, the exposed adhesive provides long-term adhesion between the catheter assembly and the patient.

Figure 2:
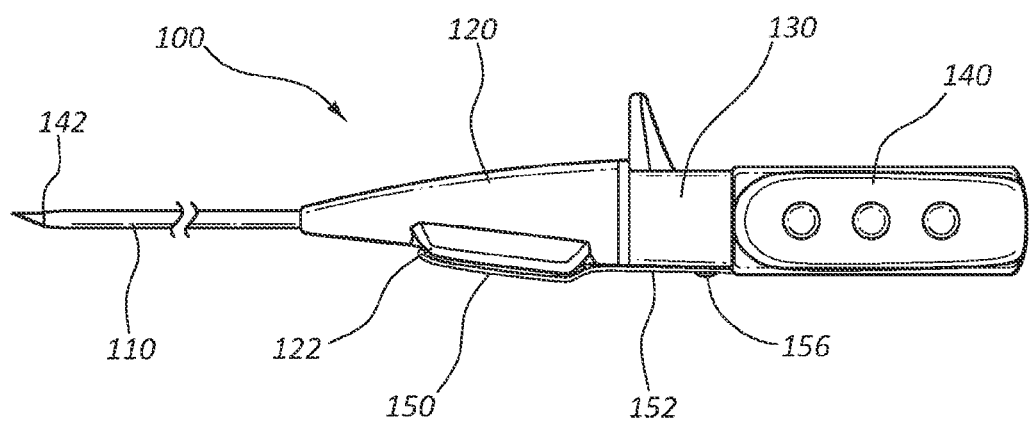
FIG. 2 illustrates a side view of the catheter assembly shown in FIG. 1.
Figure 3:
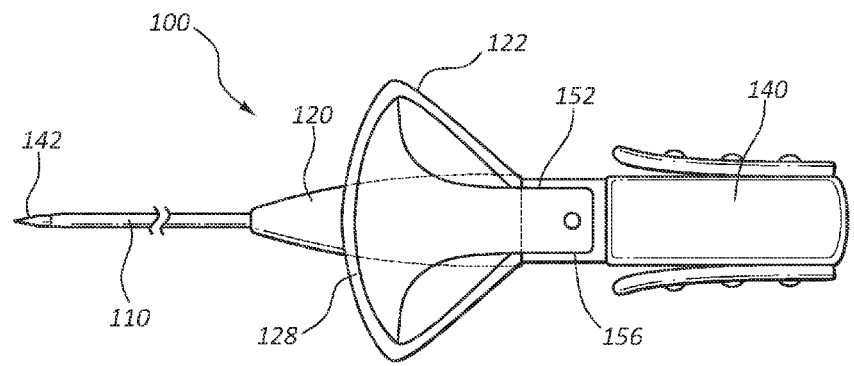
FIG. 3 illustrates a bottom view of the catheter assembly of FIG. 1.

Referring now to FIGS. 1-3, an intravenous catheter assembly 100 is shown. Intravenous catheter assembly 100 may include a catheter adapter 120 having a distal end to which is secured an intravenous catheter 110, a needle shield 130 attached to a proximal end of catheter adapter 120, and a needle hub 140 for withdrawing introducer needle 142 during placement of catheter 110. In some embodiments, catheter adapter 120 may also include a securement platform or winged extensions 122 that may interface with the skin of the patient to stabilize a desired position of catheter assembly 100 following catheterization. In some instances, winged extensions 122 may be flexible or semi-flexible to allow winged extensions 122 to contour and conform to the surface of the patient. Winged extensions 122 may further prevent catheter assembly 100 from rolling about the central axis of catheter adapter 120 when placed on patient's skin.

In some embodiments, winged extensions 122 may also include one or more adhesive portions 160 which are positioned on the underside 128 of extensions 122. Adhesive portions 160 may be positioned so as to maintain a desired position of catheter adapter 120 following catheterization. In some embodiments, release liner 150 may be placed over adhesive portions 160 to preserve the adhesive properties and sterility of adhesive portions 160 prior to securement to the patient.

Adhesive portions 160 may include any type or form of adhesive that is suitable for use with the methods and embodiments discussed. For example, adhesive portions 160 may be a spray-on adhesive, adhesive film, or any other type of adhesive application. Further, in some embodiments adhesive portion 160 may be formed of or include a polymer-based pressure sensitive adhesive. As such, a bond is formed between adhesive portion 160 and the patient's skin by applying light pressure between winged extension 122 and the skin. Adhesive portion 160 may further include a slight liquid carrier that facilitates bonding with the skin. In some instances, adhesive portion 160 may include a single-use glue, such that the adhesive strip loses its adhesive properties once removed from the skin. In some embodiments, adhesive portions 160 may also include an anti-microbial agent to aid in maintaining a sterile intravenous insertion site.

In other instances, adhesive portion 160 may be formed of or include a multiple-use glue, wherein the adhesive strip may be applied repeatedly to the skin of the patient. For example, a multiple-use glue may be desired to permit subsequent adjustment of the catheter assembly's position following securement with adhesive portions 160. This may be desirable for situations where the tip of the catheter becomes occluded within the vein, thereby requiring the catheter 110 to be moved slightly to reestablish patency. This may also be a desirable feature where the placement of the catheter assembly 100 becomes uncomfortable to the patient.

Release liner 150 may generally be provided as a protective layer that is applied over adhesive portion 160 to preserve the adhesive properties of portion 160 prior to use. A distal end 152 (or pull tab) of release liner 150 may be attached to needle shield 130 at attachment 156. Release liner 150 may be attached to needle shield 130 with any suitable device or method. For example, distal end 152 may be uncoated with a release agent, or may include other agents to permit adhesion to needle shield 130 using an adhesive. In other embodiments, distal end 152 may be attached at attachment 156 with sonic welding, heat bonding, or other suitable manufacturing technique. Similarly, attachment 156 may include a mechanical fastener such as a button, rivet, screw, etc.

Release liner 150 may be formed and placed such that it may be folded over to cover adhesive portion 160 and extend to attachment 156 on needle shield 130. The attachment of release liner 150 to needle shield 130 may provide an automatic removal of release liner upon placement of catheter 100 and removal of introducer needle 142 for easy and convenient positioning of catheter adapter 120 without the need for additional materials. The automatic release functionality will be discussed in further detail below. In some embodiments, distal end 152 of release liner 150 may be attached to needle hub 140, such that separation of needle hub 140 from catheter adapter 120 automatically peels release liner away from and exposes adhesive portions 160.

Release liner 150 may also prevent premature securement of catheter assembly 100 to the patient, thereby allowing the clinician to freely move and position catheter assembly 100 prior to withdrawal of introducer needle 142 and final securement. In some embodiments, adhesive portions 160 and release liner 150 are positioned on catheter assembly 100 such that the clinician's technique is not hindered, or does not require adjustment when inserting catheter assembly 100 into the patient. Thus, a clinician may utilize the same technique for inserting catheter assembly 100 into a patient regardless of whether or not the clinician utilizes adhesive portions 160 to secure catheter assembly 100 to the patient.

Release liner 150 may include any material or combination of materials that permit temporary bonding between release liner 150 and adhesive portion 160, wherein upon removal of release liner 150 from adhesive portion 160, the adhesive is left undisturbed. Non-limiting examples of compatible materials for release liner 150 include plastic film, paper, plastic, metal foil, plastic coated paper, wax coated paper, wax coated plastic, plastic coated foil, and wax coated foil. Similarly, release liner 150 may be coated, impregnated, or layered with a release agent. In some embodiments, only on the portion of release liner in contact with adhesive portion 160 may have the release properties or agents.

Figure 4:
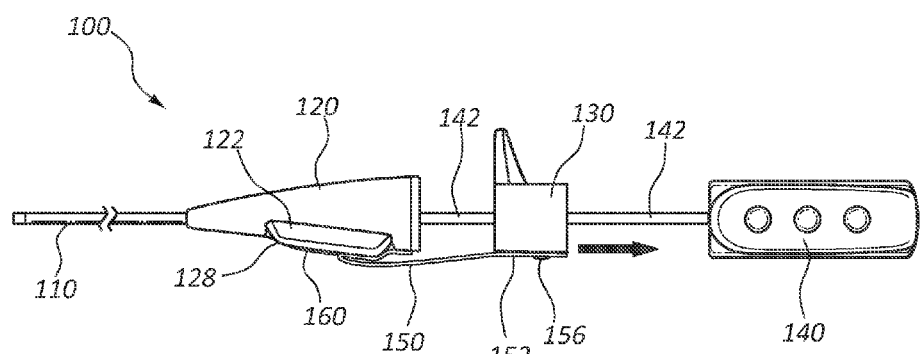
FIG. 4 illustrates a side view of the catheter assembly of FIG. 1, further illustrating a partially removed release liner as the introducer needle is withdrawn from the catheter assembly, thereby exposing the adhesive portion of the catheter assembly.
Figure 5:
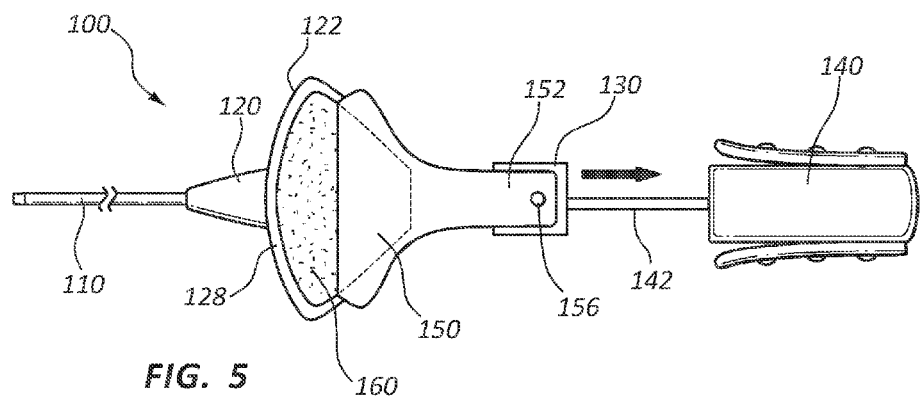
FIG. 5 illustrates a bottom view of the catheter assembly of FIG. 1, further illustrating a partially removed release liner as the introducer needle is withdrawn from the catheter assembly, thereby exposing the adhesive portion of the catheter assembly.

Turning now to FIGS. 4 and 5, catheter assembly 100 may provide for an automatic release of release liner 150 when needle hub 140, needle shield 130 and introducer needle 142 are removed during placement of catheter 110 and catheter adapter 120. Introducer needle 142 may extend from a distal end of catheter 110 to provide a sharp and rigid element to pierce the skin of a patient and position the distal end of catheter 110 within the vascular system of the patient. Once catheter 110 is intravenous, needle hub 140 may be separated from needle shield 130 to withdraw introducer needle 142 from catheter 110. Needle shield 130 may provide a safety cap for introducer needle 142 to avoid inadvertent sticks with the withdrawn introducer needle. As such, needle shield 130 is also detached from catheter adapter 120 upon withdrawal of introducer needle 142, and needle hub 140, needle shield 130 and introducer needle 142 may then be disposed of.

As discussed above, distal end 152 of release liner 150 may be attached to needle shield 130 at attachment 156. When introducer needle 142 is withdrawn, taking needle shield 130 along with it, distal end 152 may be pulled and release layer thereby peeled back to reveal adhesive portion 160. Once the introducer needle 142 and needle shield 130 are completely removed, release liner 150 may also be completely detached from adhesive portion 160, permitting adhesion of catheter adapter 120 to a patient. In some embodiments, the adhesive portion 160 may provide a temporary attachment, allowing a clinician to use both hands in acquiring and placing more long-term securements to hold catheter 110 and catheter adapter 120 in place.

Figure 6:
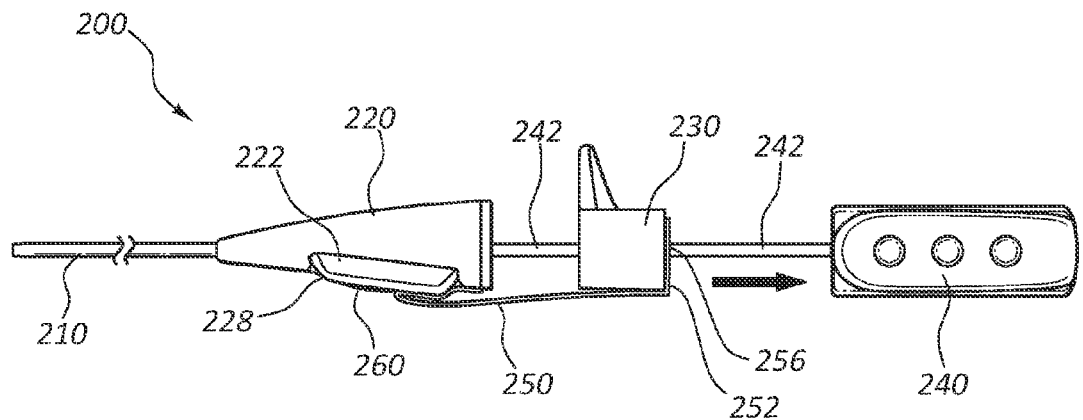
FIG. 6 illustrates a side view of an exemplary catheter assembly illustrating a partially removed release liner as the introducer needle is withdrawn from the catheter assembly, thereby exposing the adhesive portion of the catheter assembly.

Turning to FIG. 6, Similar to catheter assembly 100, discussed above, catheter assembly 200 may include a catheter adapter 220 having a distal end to which is secured an intravenous catheter 210, a needle shield 230 attached to a proximal end of catheter adapter 220, and a needle hub 240 for withdrawing introducer needle 242 during placement of catheter 210. Catheter adapter 220 may also include a securement platform or winged extensions 222 and one or more adhesive portions 260 which are positioned on the underside 228 of extensions 222. Adhesive portions 260 may be positioned so as to maintain a desired position of catheter adapter 220 following catheterization. Release liner 250 may be attached to introducer needle 242 such that removal of introducer needle 242 automatically peels release liner away from and exposes adhesive portions 260. For example, distal end 252 may include hole 256 through which introducer needle 242 passes. Distal end 252 of release liner 250 may be between needle shield 230 and needle hub 240, such that when needle shield 230 is removed, release liner 250 is automatically peeled away to reveal adhesive portion 260.

Figure 7:
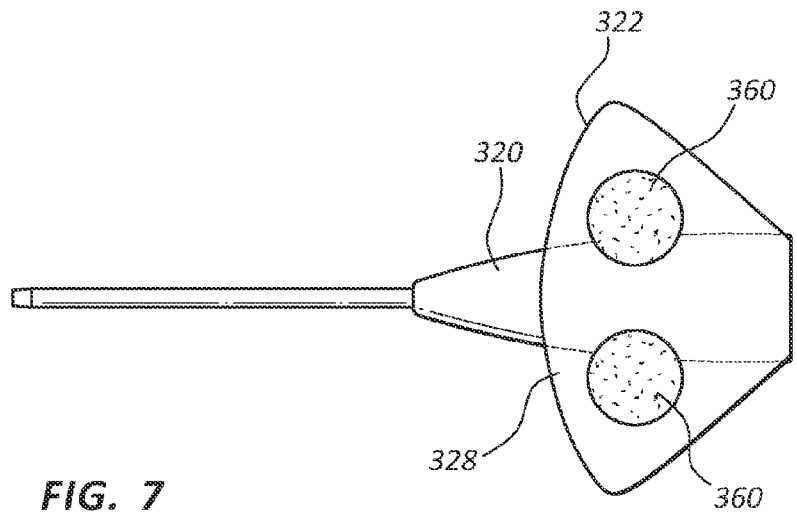
FIGS. 7 and 8 illustrate bottom views of embodiments of catheter adapters with different adhesive patterns.
Figure 8:
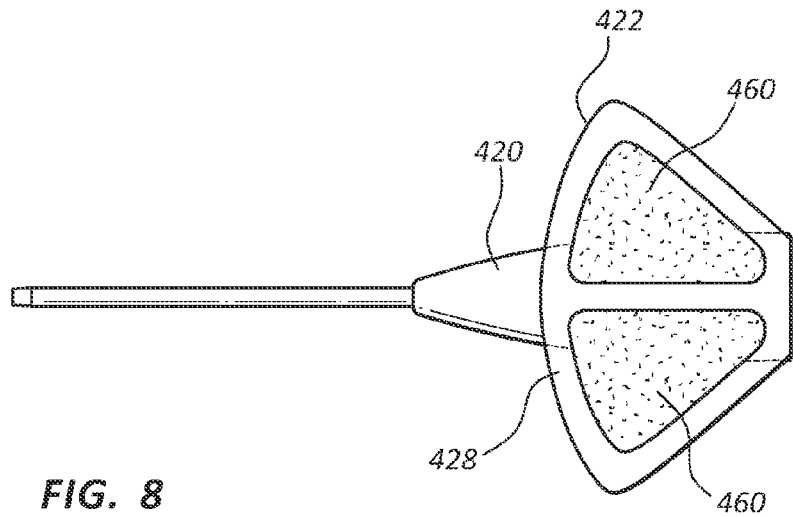

Turning to FIGS. 7-8, the adhesive portion may be formed any shape, pattern, size and/or configuration necessary to provide a desired adhesion between the catheter adapter and the skin of the patient. For example, as shown in FIG. 7, adhesive portions 360 may be placed on the underside 328 of winged extensions 322 of catheter adapter 320 and generally formed as circles on each of the winged extensions 322. This form may be advantageous when manufacturing the catheter adapter 320 as some suitable adhesives may be deposited as a drop of fluid, allowing a simple manufacturing step to provide adhesive portions 360 for use as described above. Similarly, as shown in FIG. 8, adhesive portions 460 on underside 428 of winged extensions 422 of catheter adapter 420 may be formed in as irregular patches on each of the winged extensions 422.

Other embodiments may include adhesive portions formed in a single line or plurality of parallel lines. In other embodiments, the adhesive portions may include several circles or other desired shapes and configurations. Further, in some embodiments adhesive portion 160 may cover the entire underside 128 of winged extensions 122, or a desired portion of the underside 128. For example, depending on the type of adhesive used, it may be desirable to cover a percentage of the underside 128 with adhesive to ensure sufficient securement when used. In some embodiments, the coverage may be between 10% and 100% of the underside 128 of winged extensions 122. For stronger adhesives, as smaller percentage of coverage may be sufficient, while a weaker adhesive may require a larger percentage. Similarly, for larger or smaller catheter adaptors or winged extensions, coverage may be adjusted to provide sufficient surface area of adhesion for desired securement. In some embodiments, such as shown in FIG. 5, about 80% coverage may be provided. Alternatively, as shown in FIG. 7, about 15%, or about 50% as shown in FIG. 8.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. An intravenous catheter assembly, comprising:
   a catheter adapter;
   a catheter coupled to an end of the catheter adapter;
   at least one adhesive portion affixed to the catheter adapter;
   a release liner covering the at least one adhesive portion; and a releasable component coupled to the catheter adapter that is configured to be removed from the catheter adapter, wherein the release liner is coupled to the releasable component so that upon removing the releasable component from the catheter adapter, the release liner is removed from the at least one adhesive portion.

2. The assembly of claim 1, wherein the catheter adapter further comprises a winged extension, and wherein the adhesive portion is affixed to the winged extension.

3. The assembly of claim 2, wherein the at least one adhesive portion is affixed on a bottom side of the winged extension configured to contact the skin of a patient when in use.

4. The assembly of claim 3, wherein at least 50% of the bottom side of the winged extension is covered by the at least one adhesive portion.

5. The assembly of claim 1, wherein the releasable component is a needle shield.

6. The assembly of claim 1, wherein the release liner is folded over.

7. The assembly of claim 1, wherein the adhesive includes an anti-microbial agent.

8. A catheter assembly, comprising:
   a catheter adapter having an outer surface;
   an adhesive affixed to the outer surface;
   a release liner releasable coupled to the adhesive; and
   a releasable component coupled to the catheter adapter, the release liner being coupled to the releasable component such that the releasable component pulls the release liner from the adhesive when the releasable component is separated from the catheter adapter.

9. The assembly of claim 8, wherein the release liner comprises a folded configuration prior to use.

10. The assembly of claim 8, wherein the catheter adapter comprises winged extensions forming the outer surface.

11. The assembly of claim 8, further comprising a catheter coupled to the catheter adapter, and wherein the releasable component is configured to aid in placement of the catheter adapter intravenously.

12. The assembly of claim 8, wherein the releasable component is one of an introducer needle, a needle shield, or a needle hub.

13. A catheter assembly, comprising:
    a catheter adapter having a proximal end, a distal end and a middle section extending therebetween;
    a securement platform coupled to the middle section and comprising an underside;
    an adhesive applied to the underside of the securement platform;
    a needle assembly configured to be removed from the catheter adapter; and
    a release liner applied to the adhesive, the release liner having a pull tab that is attached to the needle assembly so that when the needle assembly is removed from the catheter adapter, the release liner is removed from the adhesive.

14. The assembly of claim 13, wherein the needle assembly comprises a needle shield and an introducer needle.

15. The assembly of claim 14, wherein the pull tab is coupled to one of the needle shield and the introducer needle.

16. The assembly of claim 13, wherein the adhesive comprises at least 50% of the underside.

17. The assembly of claim 13, wherein the release liner is in a folded configuration.

18. The assembly of claim 17, wherein the adhesive comprises an anti-microbial agent.

19. The assembly of claim 13, wherein the adhesive comprises a single-use glue.

20. The assembly of claim 13, wherein the adhesive comprises a multiple-use glue.

* * * * *